United States Patent [19]

Cornils et al.

[11] Patent Number: 4,593,126
[45] Date of Patent: Jun. 3, 1986

[54] PROCESS FOR PREPARING ALDEHYDES

[75] Inventors: Boy Cornils, Dinslaken; Werner Konkol, Oberhausen; Hanswilhelm Bach, Duisburg; Georg Dambkes, Dinslaken; Wilhelm Gick, Duisburg; Wolfgang Greb, Dinslaken; Ernst Wiebus, Oberhausen; Helmut Bahrmann, Hunxe, all of Fed. Rep. of Germany

[73] Assignee: Ruhrchemie Aktiengesellschaft, Fed. Rep. of Germany

[21] Appl. No.: 719,754

[22] Filed: Apr. 4, 1985

[30] Foreign Application Priority Data

Apr. 10, 1984 [DE] Fed. Rep. of Germany ....... 3413427

[51] Int. Cl.$^4$ .............................................. C07C 45/50
[52] U.S. Cl. ..................................... 568/454; 568/451
[58] Field of Search ................................ 568/454, 451

[56] References Cited

U.S. PATENT DOCUMENTS

| Re. 31,812 | 1/1985 | Kuntz | 568/454 |
| 4,248,802 | 2/1981 | Kuntz | 568/454 |
| 4,510,332 | 4/1985 | Matsumat | 568/454 |

FOREIGN PATENT DOCUMENTS

| 2627354 | 12/1976 | Fed. Rep. of Germany | 568/454 |
| 5041805 | 4/1985 | Japan | 568/454 |
| 12314910 | 12/1977 | France | 568/454 |

*Primary Examiner*—Werren B. Lone
*Attorney, Agent, or Firm*—Bierman, Peroff & Muserlian

[57] ABSTRACT

A process for the hydroformylation of aldehydes comprising reacting aliphatic olefins with carbon monoxide and hydrogen in a liquid phase in the presence of water, a rhodium catalyst and a water soluble salt of a sulfonated or carboxylated triarylphosphine, the reaction taking place in the presence of an aqueous phase having a pH of about 5.5 to about 6.2.

13 Claims, No Drawings

PROCESS FOR PREPARING ALDEHYDES

The present invention relates to hydroformylation reactions utilizing rhodium catalysts. It is especially directed to the production of aldehydes from olefins and synthesis gas (carbon monoxide and hydrogen) using a water soluble rhodium complex catalyst.

It is well known that aldehydes and alcohols can be synthesized from olefins, carbon monoxide, and hydrogen. These reactions are conducted catalytically using hydridometal carbonyl compounds as catalysts. The metal atom of the hydridometal carbonyl is preferably selected from Group VIII of the Periodic Table. One of the most important of these metals, used on a large industrial scale, is cobalt, although recently rhodium has been rapidly growing in importance.

The cobalt catalyzed reaction takes place at relatively higher pressures, while the rhodium mediated hydroformylation can be conducted at much lower pressures, thereby resulting in energy and equipment savings. Still further, the rhodium catalyzed process is much more selective than the cobalt induced process; rhodium catalysts lead to the formation of primarily straight n-aldehydes, with iso-aldehydes being formed to only a very minor extent. Additionally, side reactions, such as hydrogenation of the olefin to a saturated hydrocarbon, occur to a much lesser extent with rhodium catalysts as compared to cobalt catalysts.

In typical industrial process applications, rhodium catalysts are used as modified hydridorhodium carbonyls. Generally, these catalytic agents contain additional ligands; in some cases, they have excess ligands present. Particularly suitable ligands have been tertiary phosphines or phosphites. One major advantage of these ligands is that the hydroformylation reaction pressure can be reduced to below 300 bars ($30 \times 10^3$ kPa).

Unfortunately, such processes have problems of separating the reaction products and recovering the catalysts homogeneously dissolved therein. Usually, the raw reaction product mixture is distilled so as to recover the desired reaction product. However, this method can only be employed on a practical level when the olefin reactant is a lower olefin, i.e. has 5 carbons or less. This is primarily due to the thermal sensitivity of the resultant aldehydes and alcohols derived from higher olefin starting materials. In addition, thermal loading of the distillate leads to decomposition of the rhodium complex compounds and substantial losses of catalyst.

Many of these problems are avoided with the utilization of water-soluble catalyst systems. Since the catalyst is water-soluble and the desired organic products are not, there is a natural tendency for the desired products and catalyst to separate into organic and aqueous phases, respectively. Separation of the phases can then be achieved by non-thermal means.

Some typical water-soluble rhodium catalysts are described in German Pat. No. 26 27 354. In that disclosure, rhodium catalyst water solubility is achieved by complexation with sulfonated triarylphosphines. In addition to the sulfonated triarylphosphines, carboxylated triarylphosphines may also be employed.

The hydroformylation reaction takes place in the aqueous phase, which contains the catalyst. Hence, the reaction is highly dependent upon the reactants reaching the aqueous phase. According to the aforementioned German Patent, the pH of the aqueous catalyst solution can vary widely. This disclosure states that the pH should be no less than 2, preferably 2–13, and most preferably 4–10. Even within this range, conversion and selectivity have been found to vary widely.

It is an object of the present invention to overcome the above defects.

It is another object to provide a process for hydroformylation which results in high conversion and selectivity while still permitting simple separation and recovery of catalyst and reaction product.

Surprisingly, these and other objects are achieved by observing a very limited pH range for the catalyst solution. In general, the invention is a hydroformylation process of reacting olefins, preferably having 2–12 carbon atoms, with carbon monoxide and hydrogen. The reaction takes place in a liquid phase in the presence of water, a rhodium catalyst and a complexing agent. The rhodium can be present as a metal or a compound, preferably a hydridocarbonyl compound. The complexing agent is a water-soluble salt capable of complexing with the rhodium catalyst and is preferably a sulfonated or carboxylated triarylphosphine. Of course, the rhodium catalyst and the complexing agent need not exist as two separate entities, but may be preformed into a single complex. The aqueous solution containing the catalyst must have a pH of about 5.5 to about 6.2; it is more preferably about 5.8 to about 6.0.

To be more precise, the catalyst solution referred to above is the aqueous phase during the hydroformylation reaction. In essence, it is a solution of the catalyst and the complexing agent.

The pH of the aqueous phase is monitored by any suitable method; typically, one will conduct measurements using suitable electrodes. The pH of the solution is generally set during preparation of the complexing agent, since rhodium and rhodium compounds which are subsequently added have no significant effect on it.

The preferred sulfonated triarylphosphines can be prepared by sulfonating triarylphosphines with oleum, diluting with product with water, and extracting the sulfonated triarylphosphine with a water-insoluble amine in a water-insoluble organic solvent. Treating the extract with an aqueous solution of a base, transfers the sulfonated triarylphosphine back into an aqueous phase. Precise amounts of aqueous basic solution added to the organic phase can simultaneously regulate the pH to the proper range.

Of course, it is equally possible to obtain the desired pH-value in weakly alkaline to weakly acidic catalyst solutions by the addition of acids. For this purpose, inorganic acids, such as phosphoric acid or sulphuric acid; acidic salts of multivalent inorganic acids, such as alkali metal hydrogen sulphates; as well as water-soluble organic acids, e.g. formic acid, acetic acid, propionic acid, butyric acid are useful examples. Other such acids will be known to those in the art. Furthermore the pH value can be adjusted with the aid of a buffer mixture of salts, preferably of inorganic oxyacids. Depending on the pH range required, the systems $Na_2HPO_4/KH_2PO_4$ or $KH_2PO_4$/borax are particularly preferred buffer mixtures; however, any buffer system which yields the appropriate pH and does not interfere with the reaction is suitable.

It has been found that the reaction selectivity drops considerably when our upper pH limit is exceeded. Beyond this range, the conditions favor aldolization. Those pH values which are below the lower limit of the claimed range lead to a reduction in catalyst activity.

In the process according to the invention, olefins in general, and preferably those having 2 to 12 carbon atoms, can be hydroformylated. These olefins can be linear or branched and have a terminal or non-terminal double bond. Examples of preferred olefins are: ethylene, propylene, 1-butene, 2-butene, 1-pentene, 2-methyl-1-butene, 1-hexene, 2-hexene, 1-heptene, 1-octene, 3-octene, 3-ethyl-1-hexene, 1-decene, 3-undecene, 4,4-dimethyl-1-nonene, 1-dodecene. Linear olefins with 2 to 8 carbon atoms, such as ethylene, propylene, 1-butene, 1-pentene, 1-hexene, 1-heptene, and 1-octene, are especially preferred.

Rhodium is used as a catalyst in metallic form or in the form of one of its compounds. This is complexed with a water-soluble complexing agent, preferably a phosphine, corresponding to the general formula:

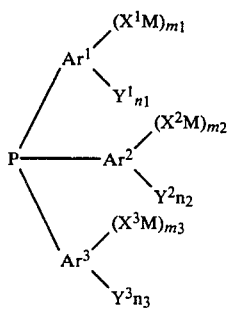

wherein $Ar^1$, $Ar^2$ and $Ar^3$ are each an aryl, preferably a phenyl or naphthyl group; $Y^1$, $Y^2$, and $Y^3$ are each independently straight or branched alkyl having 1 to 4 carbon atoms, alkoxy, preferably having 1-4 carbon atoms, halogen, OH, CN, $NO_2$, or $R^1R^2N$, in which $R^1$ and $R^2$ are each independently straight or branched alkyls having 1 to 4 carbon atoms; $X^1$, $X^2$, and $X^3$ are each independently a carboxylate ($COO^-$) or sulphonate ($SO_3^-$); $n_1$, $n_2$, and $n_3$ are the same or different whole numbers from 0 to 5; $m_1$, $m_2$, and $m_3$ are the same or different whole numbers from 0 to 3 provided that the sum of $m_1$, $m_2$, and $m_3$ is at least 1, preferably 3; M is an alkali metal ion, an equivalent of an alkaline earth metal or zinc ion, ammonium, or quarternary alkylammonium having the general formula $N(R^3R^4R^5R^6)$ wherein $R^3$, $R^4$, $R^5$, $R^6$ are each independently straight or branched alkyls having 1 to 4 carbon atoms. It is preferred that $m_1$, $m_2$, and $m_3$ are each 1. According to a preferred embodiment, $Ar^1$, $Ar^2$, $Ar^3$ are each a phenyl group and $X^1$, $X^2$, $X^3$ are each a sulfonate group with $m_1$, $m_2$, and $m_3$ each being 1. Examples of compounds with the aforementioned general formula are triphenylphosphine-tri-(tetraalkylammonium)-trisulfonate, triphenylphosphine-tri-Na-trisulfonate, and triphenylphosphine-tri-Na-tricarboxylate. Other preferred phosphines are those wherein $Ar^1$–$Ar^3$, $Y^1$–$Y^3$, $R^1$–$R^2$, $X^1$–$X_3$, $n_1$–$n_3$, $m_1$–$m_3$, or $R^3$–$R^6$ are not chosen independently of each other, but are the same within the respective groups set forth above. Hence, $Y^1 = Y^2 = Y^3$ in one preferred form of the phosphine.

The rhodium is used either in metallic form or as a compound. When metallic rhodium is used, it is preferably applied to a carrier such as active carbon, calcium carbonate, aluminium silicate or alumina. Other suitable carriers will be known to those in the art as will methods of using metallic rhodium without a carrier. Suitable rhodium compounds are substances which are water-soluble under the reaction conditions. Typical materials in this class are the various rhodium oxides, salts of inorganic hydrogen and oxyacids as well as salts of aliphatic mono and polycarboxylic acids. Examples of these compounds include rhodium chloride, rhodium nitrate, rhodium sulfate, rhodium acetate, rhodium malonate. Furthermore, rhodium carbonyl compounds such as tricarbonyl rhodium or tetracarbonyl rhodium or complex rhodium salts, e.g. cyclo-octadienyl rhodium chloride can also be used. Rhodium oxide, rhodium chloride and rhodium acetate are preferred.

The catalyst solution can be prepared in advance, e.g. from aqueous phosphine solution and the required amount of rhodium, and then fed into the reaction zone. However, it is also possible to prepare the catalyst in the reaction zone by simply mixing the components thereof.

The rhodium concentration in the aqueous catalyst solution is preferably 10 to 2000 weight ppm, based on the solution. The water-soluble complexing agent, preferably phosphine, is used in an amount of 1 to 1000 mole, preferably 2 to 300 mole, per 1 gram-atom of rhodium.

The total pressure of the hydrogen and carbon monoxide is 1 to 200 bar (100 to $20 \times 10^3$ kPa), preferably 10 to 100 bar ($1 \times 10^3$ to $10 \times 10^3$ kPa). The composition of the synthesis gas, i.e. the ratio of carbon monoxide to hydrogen, can be varied within a wide range. Generally, a synthesis gas is used in which the volume ratio of carbon monoxide to hydrogen is 1:1 or deviates only minimally from this value. The reaction takes place at temperatures of 20° C. to 150° C. and can be carried out either continuously or discontinuously.

The following examples illustrate, but do not limit, the scope of the invention.

EXAMPLE 1

600 weight ppm of rhodium aqueous, phosphine containing solution (based on the aqueous solution) and as much propylene as necessary to maintain a constant partial pressure of propylene, CO and $H_2$ in a ratio of 2:1:1, in accordance with the olefin conversion, are reacted in a continuously operated 50 liter stirred reactor. The reaction temperature is 125° C. and the total pressure is 50 bar ($5 \times 10^3$ kPa). When a catalyst solution with a pH value of 5.9 is used, 4.6 kg propylene can be converted/per hour. The raw product obtained has the following composition:

| | |
|---|---|
| i-butanal | 3.9 weight % |
| n-butanal | 94.0 weight % |
| i-butanol | 0.1 weight % |
| n-butanol | 0.8 weight % |
| 2-ethylhexenal | 0.3 weight % |
| 2-ethylhexanal | 0.1 weight % |
| $C_8$-aldol | 0.5 weight % |
| high-boiling compounds | 0.3 weight % |

EXAMPLE 2 (COMPARISON)

Example 1 is repeated except that the pH is 6.7. In this case 4.6 kg propylene can be converted per hour. As the raw product composition below shows, the selectivity of the reaction towards the formation of n-butanal is appreciably less than in Example 1. In addition, $C_8$ aldol production is 7 times as much and high boiling compounds are produced 5 times as much as in Example 1.

| | | |
|---|---|---|
| i-butanal | 3.8 | weight % |
| n-butanal | 87.8 | weight % |
| i-butanol | 0.1 | weight % |
| n-butanol | 0.8 | weight % |
| 2-ethylhexenal | 2.2 | weight % |
| 2-ethylhexanal | 0.3 | weight % |
| C$_8$-aldol | 3.5 | weight % |
| high boiling compounds | 1.5 | weight % |

EXAMPLE 3 (COMPARISON)

Example 1 is repeated except that the pH is 5.4. In comparison with Example 1, the selectivity of the reaction towards the formation of n-butanal is essentially the same. However, the activity decreases appreciably as only 3.7 kg propylene are converted per hour, a mere 80% that of Example 1. The raw product obtained has the following composition:

| | | |
|---|---|---|
| i-butanal | 3.9 | weight % |
| n-butanal | 94.6 | weight % |
| i-butanol | 0.2 | weight % |
| n-butanol | 1.1 | weight % |
| 2-ethylhexenal | | |
| 2-ethylhexanal | 0.1 | weight % |
| C$_8$-aldol | | |
| high-boiling compounds | 0.1 | weight % |

What we claim is:

1. In a process for preparing aldehydes by reacting an olefin with carbon monoxide and hydrogen in the presence of water, a rhodium catalyst soluble in the aqueous reaction phase and a water-soluble catalyst complexing agent, said reaction takes place in a liquid phase, said water giving rise to an aqueous phase, the improvement comprising maintaining the pH of said aqueous phase in the range of about 5.5 to about 6.2.

2. The process of claim 1 wherein said pH is from about 5.8 to about 6.0.

3. The process of claim 1 wherein said olefin is selected from aliphatic olefins having 2–12 carbon atoms.

4. The process of claim 1 wherein said rhodium catalyst is selected from rhodium metal, water-soluble rhodium compounds, and rhodium carbonyl compounds.

5. The process of claim 1 wherein said complexing agent is a water-soluble salt of a carboxylated or sulfonated triarylphosphine.

6. The process of claim 5 wherein said phosphine is

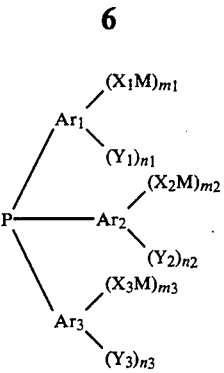

wherein $Ar_1$, $Ar_2$, and $Ar_3$ are independently phenyl or naphthyl; $X_1$, $X_2$, and $X_3$ are independently carboxylate or sulfonate; each M is independently an alkali metal ion, an equivalent of an alkaline earth metal ion or zinc ion, an ammonium ion, $N^+(R^3R^4R^5R^6)$ wherein each of $R^3$–$R_6$ is independently an alkyl having 1 to 4 carbon atoms; $Y_1$, $Y_2$, and $Y_3$ are each independently alkyl having 1 to 4 carbon atoms, alkoxy, halogen, OH, CN, NO$_2$, or $R^1R^2N$ wherein $R^1$ and $R^2$ are each independently alkyl having 1 to 4 carbon atoms; $n_1$, $n_2$, and $n_3$ are each independently an integer from 0 to 5; and $m_1$, $m_2$, and $m_3$ are independently integers from 0 to 3 provided that at least one of $m_1$, $m_2$, and $m_3$ is greater than 0.

7. The process of claim 6 wherein said $m_1$, $m_2$, and $m_3$ are all 1; said $X_1$, $X_2$, and $X_3$ are all sulfonate; and said $Ar_1$, $Ar_2$, and $Ar_3$ are all phenyl.

8. The process of claim 1 wherein said pH if adjusted with inorganic acids, acid salts of multivalent inorganic acids, or water-soluble organic acids.

9. The process of claim 1 wherein said pH is adjusted with a buffer.

10. The process of claim 9 wherein said buffer is selected from Na$_2$HPO$_4$/KH$_2$PO$_4$ and KH$_2$PO$_4$/borax.

11. The process of claim 1 wherein said rhodium is present in an amount of from about 10 to about 2000 weight ppm relative to said aqueous phase.

12. The process of claim 1 wherein said complexing agent is present in an amount of about 1 to about 1000 mole per gram-atom of rhodium.

13. The process of claim 1 wherein said reaction takes place at a temperature of about 20° to about 150° C. and a combined hydrogen and carbon monoxide pressure of about 1 to about 200 bar and said carbon monoxide and said hydrogen are utilized in a volume ratio of about 1:1.

* * * * *